(12) United States Patent
Heiden

(10) Patent No.: US 7,382,450 B2
(45) Date of Patent: Jun. 3, 2008

(54) METHOD OF DETECTING AN EDGE BEAD REMOVAL LINE ON A WAFER

(75) Inventor: Michael Heiden, Woelfersheim (DE)

(73) Assignee: Vistec Semiconductor Systems GmbH, Weilburg (DE)

( * ) Notice: Subject to any disclaimer, the term of this patent is extended or adjusted under 35 U.S.C. 154(b) by 125 days.

(21) Appl. No.: 11/387,471

(22) Filed: Mar. 23, 2006

(65) Prior Publication Data

US 2006/0238751 A1  Oct. 26, 2006

(30) Foreign Application Priority Data

Apr. 22, 2005  (DE) .................. 10 2005 018 743

(51) Int. Cl.
*G01N 21/00* (2006.01)
(52) U.S. Cl. .................. 356/237.1; 356/237.4; 356/237.5

(58) Field of Classification Search .. 356/237.1–237.6, 356/369, 238.3, 239.1–239.8, 600–613
See application file for complete search history.

(56) References Cited

U.S. PATENT DOCUMENTS

| | | | |
|---|---|---|---|
| 6,920,249 B2* | 7/2005 | Rinn et al. | 382/199 |
| 2004/0223141 A1* | 11/2004 | Rosengaus | 356/237.1 |
| 2005/0122509 A1* | 6/2005 | Backhauss | 356/237.2 |

* cited by examiner

*Primary Examiner*—Gregory J. Toatley, Jr.
*Assistant Examiner*—Tri T Ton
(74) *Attorney, Agent, or Firm*—Houston Eliseeva LLP

(57) ABSTRACT

To determine an edge bead removal line (17) on a wafer (10), first lines or edges (38, 40, 42, 44) in the edge area (19) of the wafer (10) are detected. A first line area (48) and a second line area (50) are defined on either side of these lines (38, 40, 42, 44). The structures (36) present in these edge areas (48, 50) are compared to each other. From the result of the comparison it is determined whether or not an edge bead removal line (17) is present.

9 Claims, 6 Drawing Sheets

METHOD OF DETECTING AN EDGE BEAD REMOVAL LINE ON A WAFER

RELATED APPLICATIONS

This application claims priority to German patent application number DE 10 2005 018 743.9, filed Apr. 22, 2005, which is incorporated herein by reference in its entirety.

FIELD OF INVENTION

The present invention relates to a method of detecting an edge bead removal line (EBR line) on a wafer.

BACKGROUND OF THE INVENTION

The present invention relates to a method of detecting an edge bead removal line (EBR line) on a wafer.

In semiconductor manufacture wafers are sequentially processed during the manufacturing process in a multitude of processing steps, wherein a plurality of similar, repetitive structural elements, the so-called dies, are produced on a wafer. As the integration density increases, the quality of the structures formed on the wafer is subject to increasing demands. To be able to verify the quality of the structures formed and to find defects, if any, the requirements as to the quality, the precision and the reproducibility of the components and process steps for handling the wafer are correspondingly stringent.

During the manufacturing process, photoresist layers are usually applied in the so-called spinning process, wherein the photo resist is applied near or in the center of the wafer and is spread by rotating the wafer on its surface. This process results in photoresist collecting on the edge of the wafer, the so called edge beads, which are many times thicker than the remaining photoresist layer. In order to avoid negatively affecting the manufacturing process in its subsequent processing steps and the function of the integrated circuits (ICs) to be manufactured, these edge beads have to be removed. To this end, however, they have to be reliably detected. This is why the removal of the edge beads comes to be integrated as a standard process during the manufacturing of wafers.

A method for removing and for better detecting the edge beads is disclosed for example in US2004/0223141 A1. In this document it is suggested that the contrast between the silicon layer of the wafer and an applied photoresist layer be improved by using a special illumination. To do this, the wafer has to be lighted separately with s and p polarized light in the vicinity of the Brewster angle of silicon or the photoresist layer. Subsequently the difference between the images of the reflected s polarized radiation and the image of the reflected p polarized radiation is evaluated to improve the contrast.

Since usually structures from previous processing steps are already present on the wafer, a plurality of lines or edges will be detected in the resulting gray scale image using the prior art methods. However, these may not always be easy to unequivocally associate with their cause. In particular, it is not possible to identify a certain line or edge as an edge bead removal line in an unequivocal manner.

SUMMARY OF THE INVENTION

It is therefore the object of the present invention to provide a method of detecting an edge bead removal line on a wafer, wherein the detectability on the wafer is improved.

The object is achieved according to the present invention by a method of detecting an edge bead removal line on a wafer wherein the edge of the wafer is imaged on a detector, comprising the steps of:

detecting a plurality of lines or edges in the edge area of the wafer, defining a first line area and a second line area on either side of each line or edge, determining and comparing structures in the first line area and structures the second line area with each other; and determining from the result of the comparison whether or not one of lines or edges is an edge bead removal line.

In the method according to the present invention the edge of a wafer is therefore imaged with a suitable method, in particular using dark field imaging onto a suitable detector, such as a linear array camera. The lines present on the wafer edge are detected, followed by a decision process which enables an edge bead removal line to be identified. This makes use of the fact that photoresists are transparent in the visual range of the spectrum so that the underlying structures are visible. Areas will now be defined on either side of the line or edge, and structures contained in these areas on either side of the line or edge will be compared. It will be possible to conclude from the correlation of the structures whether or not an edge bead removal line is present; because if an edge bead removal line is present, the structure underlying the photoresist will continue from one side of the line to the other side of the line.

In a preferred embodiment of the present invention the intensity profiles in the areas on either side of the line are detected, standardized if necessary, and brought into a correlation with each other. The type of standardization can also depend on the type of detector used and can comprise spectral standardization, in particular. To prevent two overlying photoresist layers or a photoresist layer on a transparent layer from negatively affecting detection, standardization can be limited by a threshold, wherein it is preferably determined that when the threshold is exceeded, no edge bead removal line is present.

The method can also be improved by selectively excluding certain lines from the comparison. This can be done in particular when it is determined that the lines or edges are due to structures in the photoresist layer.

Using the method according to the present invention it is now possible to unequivocally classify the detected lines or edges as to whether or not they are edge bead removal lines.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

Further advantages and advantageous embodiments of the present invention are the subject matter of the accompanying drawings and their descriptions wherein for clarity the drawings are not to scale.

In the drawings:

Figure 1:
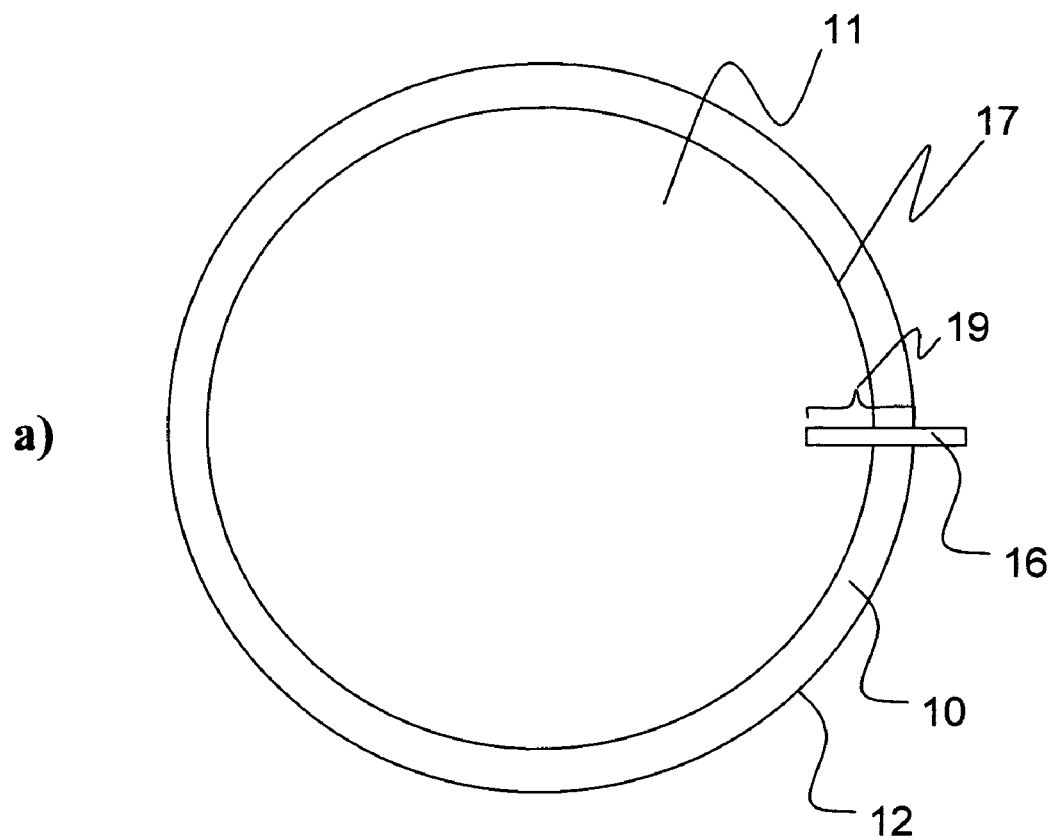
Figure 1:
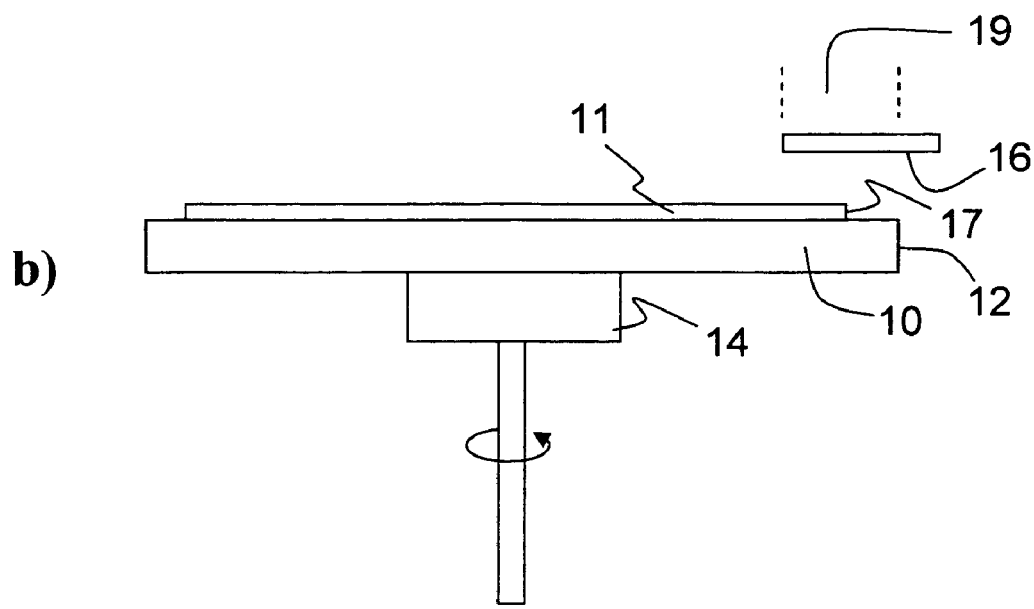
Figure 2:
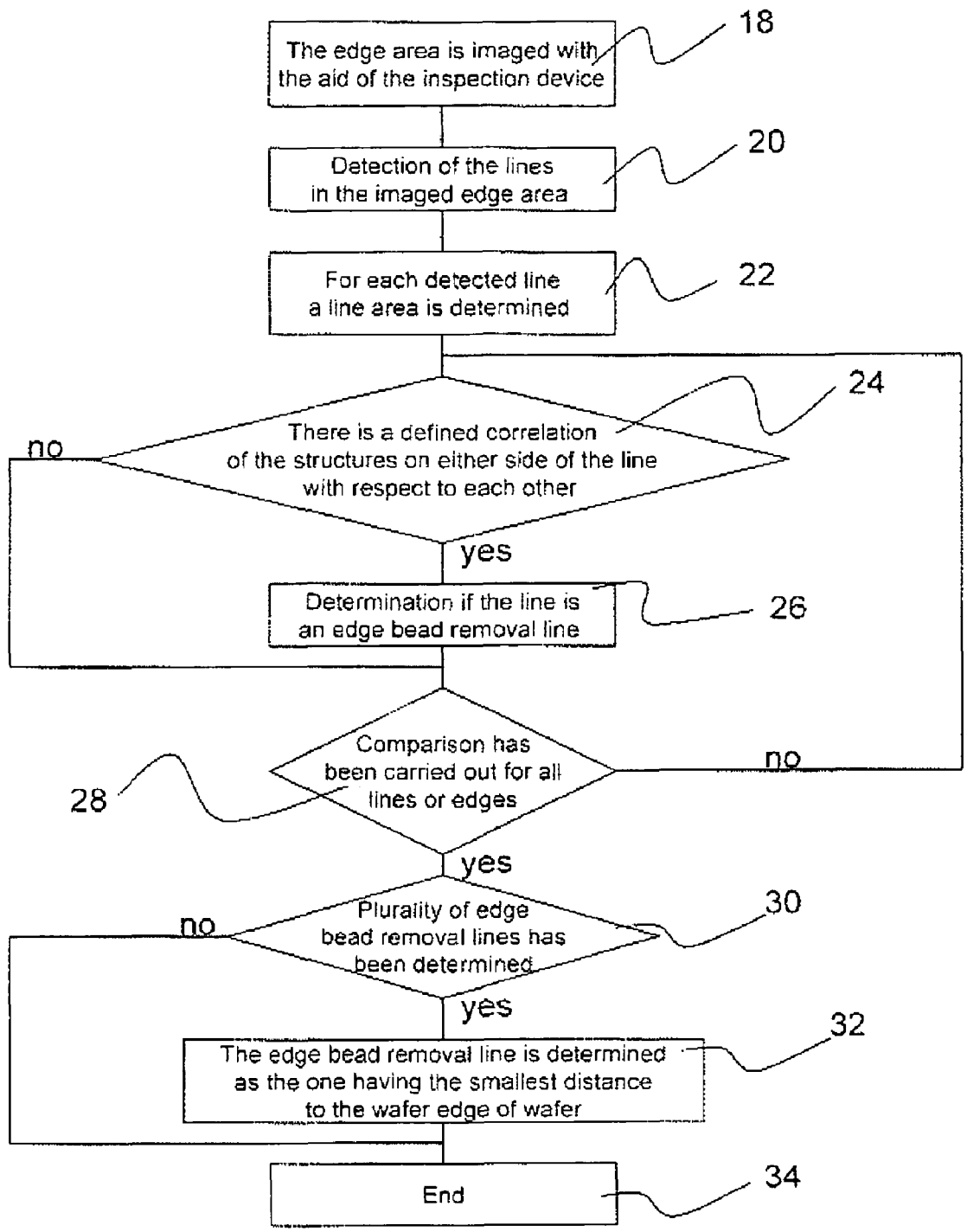
Figure 3:
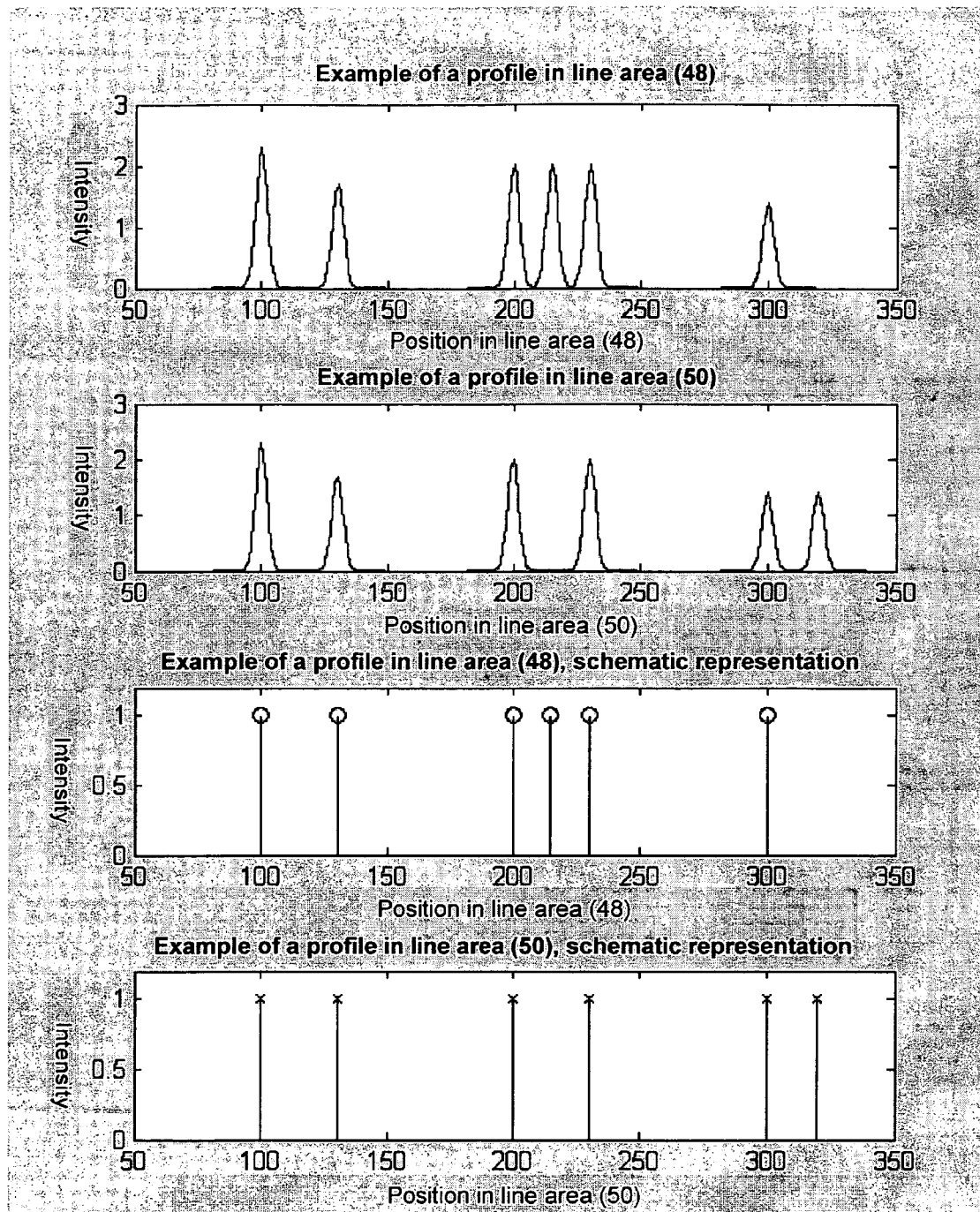
Figure 4:
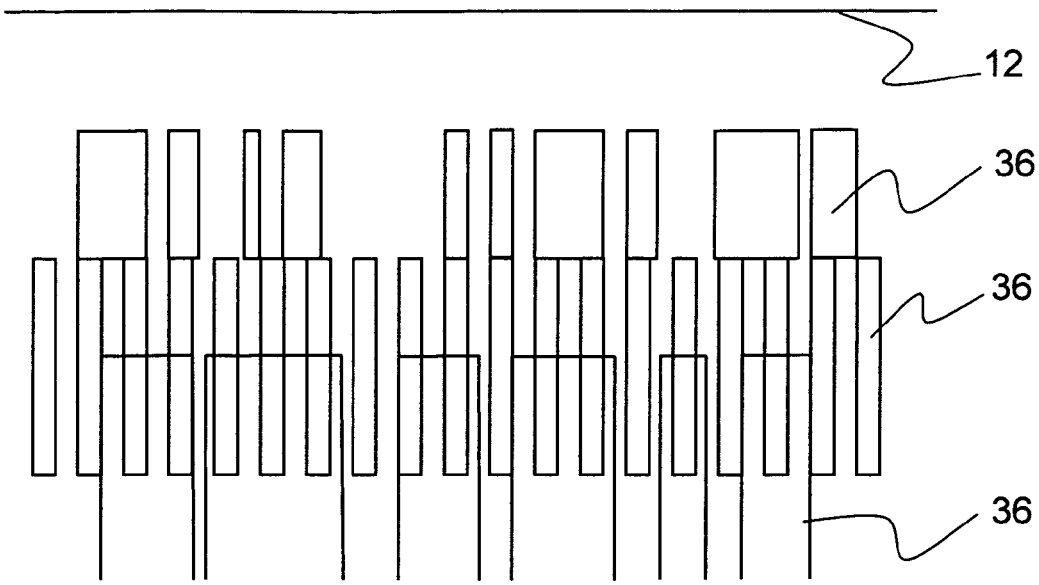
Figure 5:
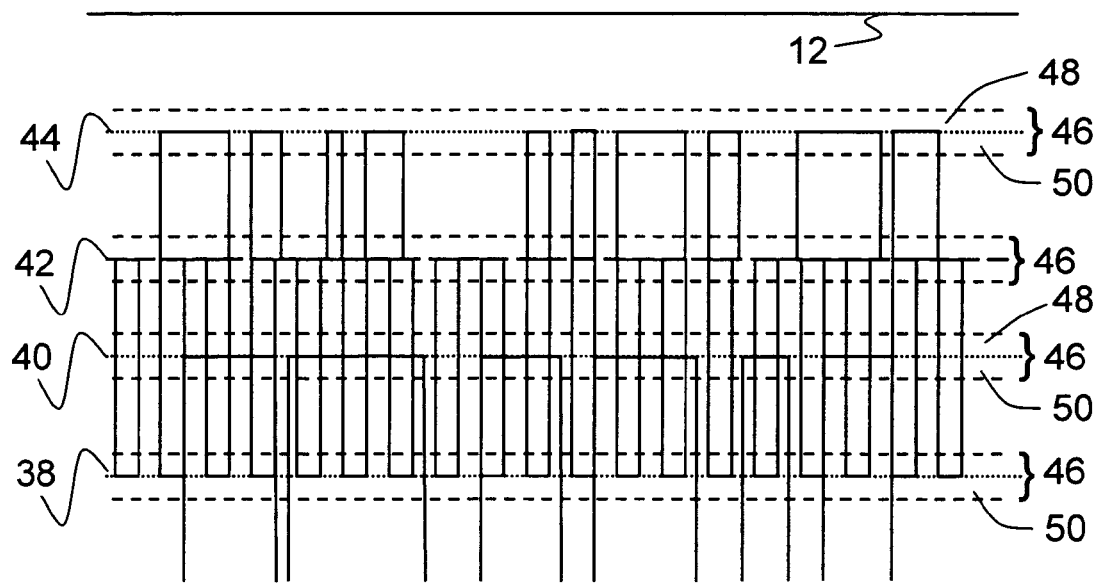
Figure 7:
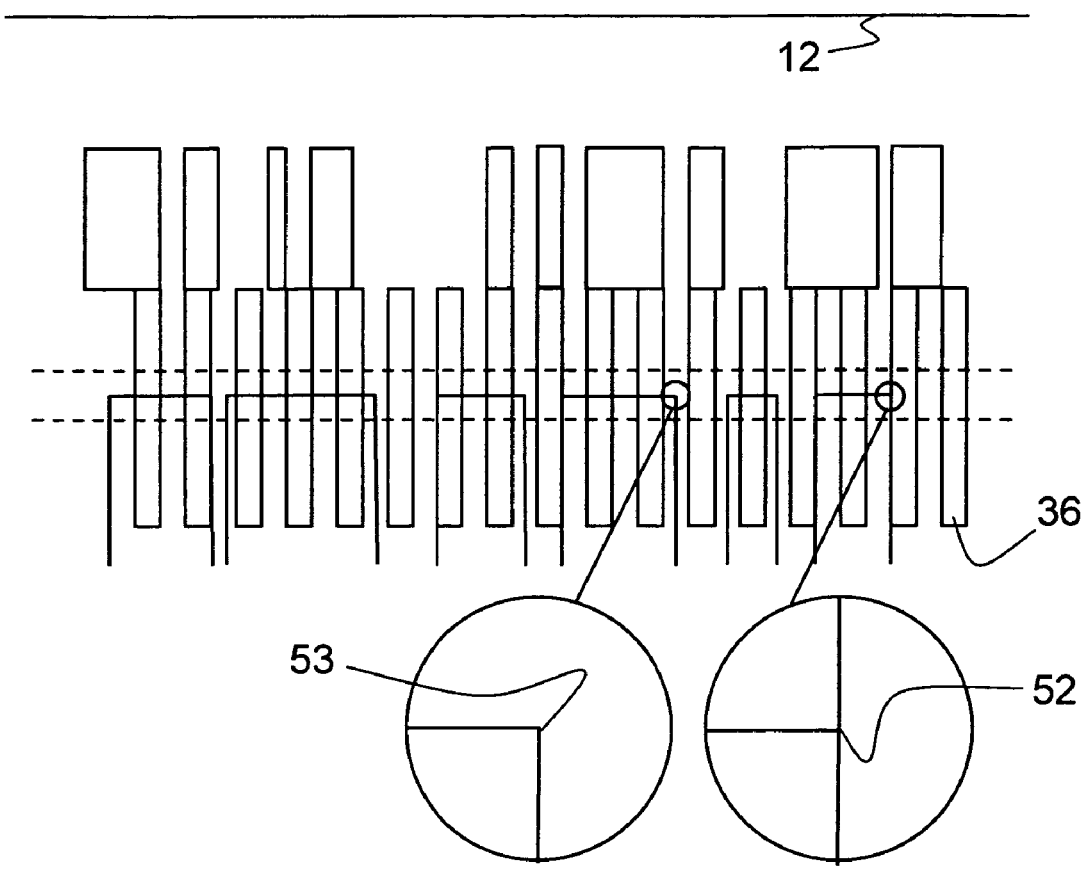
Figure 8:
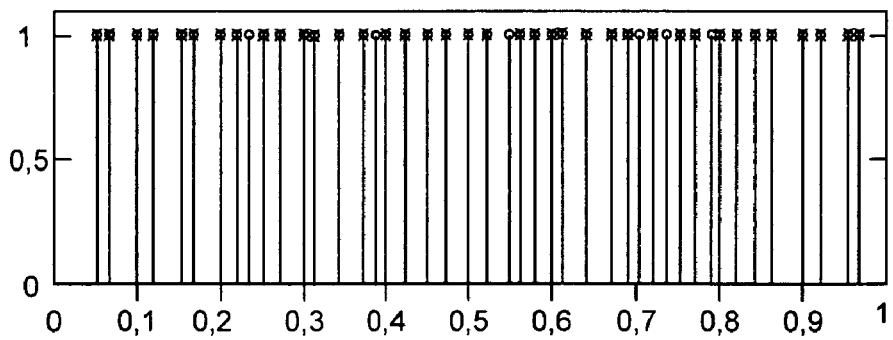

FIGS. 1a, b schematically show a measuring structure for detecting the edge bead removal line on a wafer;

FIG. 2 schematically shows the sequence of method steps according to the present invention;

FIG. 3 schematically shows the determination of the standardized intensities in the various line areas;

FIG. 4 schematically shows the areas around a wafer edge in a dark field image;

FIG. 5 schematically shows the determination of the lines and the line areas;

FIGS. 6a-d show the determination of lines within a plurality of line areas, wherein the lines or edges in each line area intersect a line running parallel to the wafer edge;

FIG. 7 schematically shows an interfering line;

FIG. 8 shows the correlation which leads to the identification of the edge bead removal line.

DETAILED DESCRIPTION OF THE PREFERRED EMBODIMENTS

FIGS. 1a and 1b schematically show the measuring structure for detecting the edge bead removal line on a wafer in top and side views. A wafer 10 having a wafer edge 12 is placed on a rotary stage 14. The wafer edge 12 rotates beneath an inspection device 16. Herein the wafer edge 12 is imaged by an imaging detector. Basically methods known from microscopy, such as bright-field, dark-field, or specialized contrast techniques can be used as imaging methods. Preferably a method is used, however, which particularly highlights the lines or edges on the wafer to be detected. This can be achieved, for example, by means of dark-field imaging. A linear array camera can be used, for example, as an inspection device 16. A photoresist layer 11 is provided on wafer 10, wherein the photoresist layer 11 does not reach the edge of wafer 12, which is why it has an edge bead removal line 17. The photoresist layer 11, together with the edge bead removal line 17, rotates past detector 16.

The sequence of method steps for detecting the edge bead removal line is schematically shown in the flow chart of FIG. 2. First, as described above, the edge area 19 is imaged in step 18 with the aid of the inspection device 16. In step 20, this is followed by a detection of the lines in the imaged edge area 19. For each detected line a line area is determined in step 22, in which, in step 24, a comparison of the structures is subsequently carried out. The determination of the line areas lying on either side of each line is more closely described with reference to FIG. 3. In step 24 the structures on either side of the line are compared with each other. Herein it is verified whether or not there is a defined correlation of the structures with respect to each other. If this is the case, it is determined in step 26 that the line is an edge bead removal line. If no correlation of the predetermined order can be determined in step 24, it is verified in step 28 whether or not the comparison has been carried out for all lines or edges. If this is not the case, a line counter is incremented by 1 and the structural comparison for this next line is carried out in step 24. After the structural comparison has been carried out for all determined lines it is checked in step 30 whether or not a plurality of edge bead removal lines has been determined. If this is not the case, the end 34 of the sequence of method steps has been reached. If a plurality of edge bead removal lines have been found, the edge bead removal line is determined in step 32 as the one having the smallest distance to the wafer edge 12 of wafer 10.

FIG. 3 schematically shows the determination of the standardized intensities in the various line areas. The wafer edge 12 rotates beneath the inspection device 16. Herein the wafer edge 12 is imaged on the imaging detector. In line area 48 and line area 50 the detector detects each line as an intensity peak which has more or less a Gaussian shape. Each intensity peak is shown as a standardized intensity represented in the form of a vertical length. During the inspection of the lengths in a line area 48, the length is followed in the direction of the wafer edge 12, and if the length extends beyond the position of the line to be found, this length is indicated at the standardized "one" with a symbol (here: a circle). In the inspection of the lengths in the line area 50 the line is also followed in the direction of the wafer edge 12 or in the direction of the line or edge to be found. If the length extends up to the position of the line or edge to be found, this length is indicated with a symbol (here: a cross) at the standardized "one".

The above sequence of method steps was described as including a determination of the line areas to be inspected for all lines before step 24. It is, of course, also possible to carry out this step for each line once the structural comparison has been carried out for the previous line.

After carrying out step 18, a line or edge image of the imaged edge area of the wafer is present in an electronic form. FIG. 4 shows a schematic example of such an obtained wafer image by means of dark-field imaging. The line 12 indicates the wafer edge. The structures 37 found on the wafer, which are present in the detected edge area of the wafer, can also be seen. As described in step 20 of FIG. 2, the edge bead removal line detection can now be carried out based on this image, wherein well known methods per se can be used.

The result is schematically shown in FIG. 5 as an example. Lines or edges 38, 40, 42 and 44 could be determined by means of the line detection 20. After the determination of the lines, it will now have to be decided which of these lines or edges 38, 40, 42, 44 corresponds to the edge bead removal line 17. According to the invention, the photoresist layer's 11 characteristic feature is used according to which the photoresist layers 11 applied to wafer 10 are transparent in the visual range of the spectrum. This means that structures 36 underlying the photoresist layers 11 can be recognized. In order to determine whether or not an edge bead removal line is present, comparison of the structures 36 in a line area 46 defined on either side of each line is carried out. The line area 46 is always subdivided in a first line area 48 on one side and a second line area 50 on the other side, wherein each line or edge 38, 40, 42, 44 is the boundary. A measure of similarity, i.e. a correlation, is determined from a comparison of the structures 36 present in either line area. It can now be decided based on this correlation whether or not the line found is an edge bead removal line 17. This is because in the case of an edge bead removal line 17 the structures 36 found underlying the edge bead removal line 17 continue from one side of the line or edge to the other side. This means that all, or almost all, lines must have both symbols on the "one" of the standardized intensity.

To determine the actual existence of an edge bead removal line an intensity profile is cut out from the recorded images both from a line area 48 on the one side and a line area 50 of the other side. The two cut-out intensity profiles are compared with each other by using a similarity function so that a correlation is obtained which represents a measure for the similarity of the structures on either side. Since the photoresist layer 11 absorbs some of the intensity it is possible that the profile is a bit darker on the side of the photoresist. This is why it may be necessary to standardize the profiles, wherein a standard measure for maximum intensity or the average intensity of the line areas can be used for example.

Figure 6:
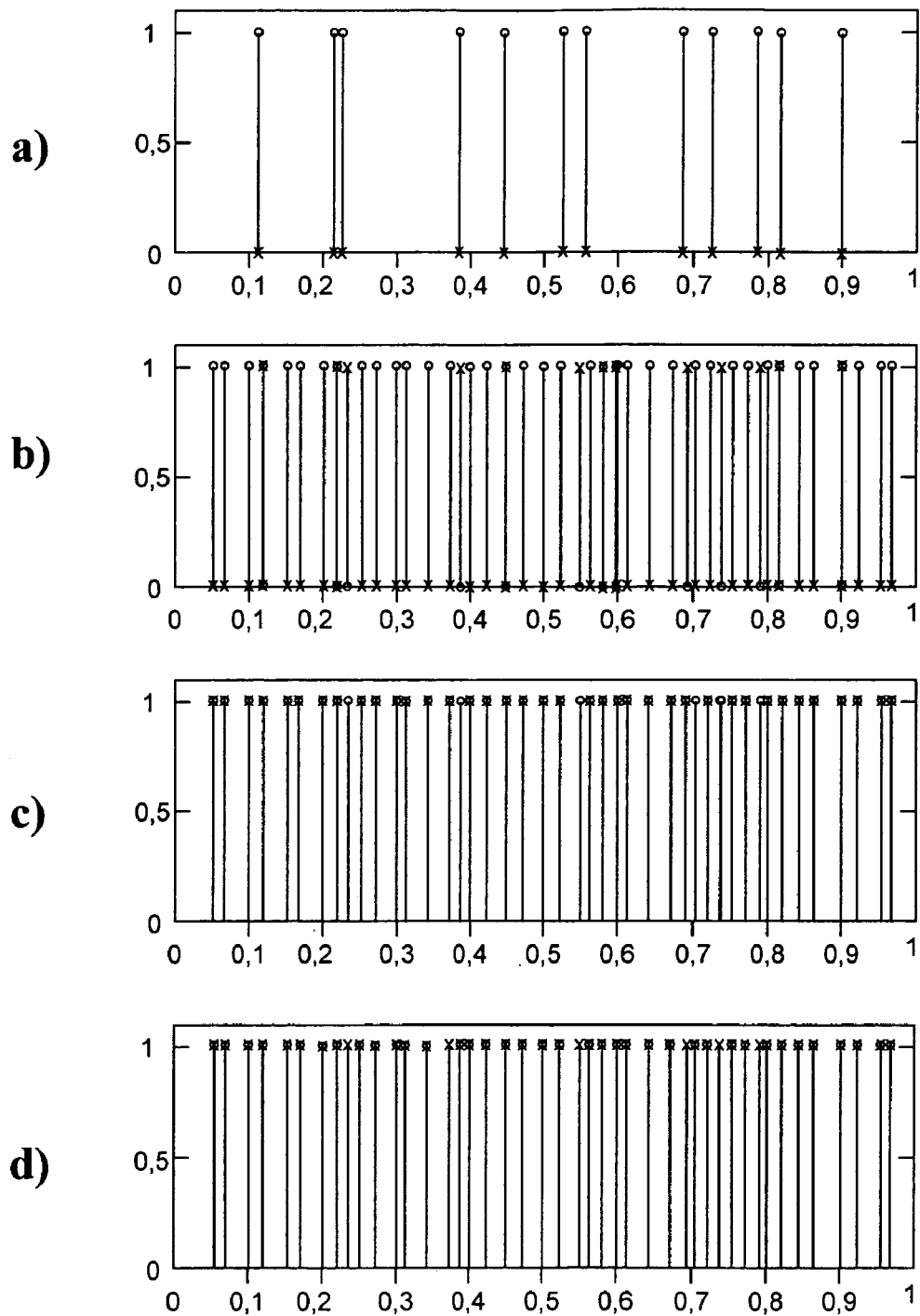

FIG. 6a shows the result for line 44. 6b shows the result for line 42. 6c shows the result for line 40. and 6d shows the result for line 38. The measure of the correlation is derived From the number of lines having both symbols on the "one". The more lines or edges there are with two symbols on the "one", the better the correlations converge on the value one, and thus the structures 36 in the individual line areas are more similar. It can be seen from FIGS. 6a-d that for lines or edges 42 and 44 there is a bad correlation so that these lines or edges are not an edge bead removal line 17. The correlation values shown in FIGS. 6c and d represent a good match, so that it can be concluded that lines or edges 38 and 40 are edge bead removal lines. The decision whether or not there is an edge head removal line 17 is therefore made based on the degree of correlation of the structures on either side of each line or edge 38, 40, 42, 44. If this correlation exceeds a certain threshold value to he determined, the line is in all probability an edge bead removal line 17. While theoretically it may be possible that the edge bead removal line runs precisely on top of a structural edge of an underlying layer, this is so improbable that this case can basically be neglected.

There is another basic possibility, that the line found is not an edge bead removal line 17 but an oxide layer, since it is also transparent. Since the layer structure is known for each wafer, the presence of oxide can be partially excluded for this reason alone. If there is still a possibility for an oxide layer to be present, it is still possible with the present method to substantially reduce the amount of data. In this case it is finally only a question of deciding whether or not the layer found is a photoresist layer or an oxide layer. This can be done, for example, by an additional subsequent inspection of the line identified as an edge bead removal line 17.

The method according to the present invention of finding an edge bead removal line can be further improved by excluding from the remaining method certain structural elements 36 as interference. To illustrate this, two structural elements 52, 53 are shown as examples in FIG. 7, which are excluded from the search for an edge bead removal line 40. In fact, structural element 53 interferes more with the determination of the correlation and therefore corrupts the result more than structural element 52. If structural elements 52, 53 are excluded from the determination of the edge bead removal line 17, i.e. in the determination of the correlation coefficient, an excellent match results as shown in FIG. 8 for line 40. Basically it is also possible for the photoresist layer 11 itself to have a structure which may compromise or corrupt the analysis of the lines or edges. By additional analysis methods, however, the presence of photoresist structures can also be excluded from the determination of the edge bead removal line 17. For this purpose the lines lying in comparison areas, i.e. in line area 48 on one side or in line area 50 on the other, can be excluded from the analysis so that they have no bearing on the correlation result.

It must also be taken into account that the result may also be corrupted if two unstructured layers overly each other. Usually these layers can be identified, however, due to their intensity development and their spectral information. In order to exclude these overlying layers from the analysis, the area of standardization can be limited, for example, by introducing a threshold. If this threshold is exceeded, it can be expected that the line is not an edge bead removal line 17 but two unstructured overlying planes.

Since lines completely covered by photoresist are also detected as edge bead removal lines with the method according to the present invention, they also have to be excluded from being identified as edge bead removal lines 17. This is done, as already described in step 32 of FIG. 2, by identifying only that line as an edge bead removal line which has the smallest distance to the wafer edge 12.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for detecting an edge bead removal line on a wafer, wherein the edge of the wafer is imaged on a detector, comprising the steps of:
   detecting a plurality of lines or edges in the edge area of the wafer,
   defining a first line area and a second line area on either side of each line or edge,
   determining and comparing structures in the first line area and structures the second line area with each other; and
   determining from the result of the comparison whether or not one of lines or edges is an edge bead removal line,
   wherein when various possible edge bead removal lines are determined, a line or edge is determined as the edge bead removal line which has the smallest distance to the edge of the wafer.

2. The method according to claim 1, wherein a first intensity profile is determined from the first line area and a second intensity profile is determined from the second line area, and the first intensity profile is correlated with the second intensity profile with the aid of a similarity function.

3. The method according to claim 2, wherein the first intensity profile and the second intensity profile are standardized in particular to the maximum intensity or the average intensity of the profiles.

4. The method according to claim 3, wherein for detecting the profiles an inspection device, in particular a CCD sensor is used, and the profiles are spectrally standardized depending on the inspection device.

5. The method according to claim 3, wherein the area in which the standardization is carried out is limited by a threshold and in that when the threshold is exceeded it is determined that no edge bead removal line is present.

6. The method according to claim 1, wherein for determining whether or not an edge head removal line is present, a subsequent inspection is carried out.

7. The method according to claim 1 wherein lines are selectively excluded from the comparison.

8. The method according to claim 7, wherein those lines or edges are excluded from the comparison for which it is determined that they are due to a structuring of the photoresist layer.

9. The method according to claim 1, wherein the edge area of the wafer is optically imaged in particular by dark-field imaging onto an inspection device.

* * * * *